(12) United States Patent
Chen et al.

(10) Patent No.: US 9,211,416 B2
(45) Date of Patent: Dec. 15, 2015

(54) CHARGING SYSTEM FOR AN IMPLANTABLE MEDICAL DEVICE EMPLOYING MAGNETIC AND ELECTRIC FIELDS

(71) Applicant: Boston Scientific Neuromodulation Corporation, Valencia, CA (US)

(72) Inventors: Joey Chen, Valencia, CA (US); Robert Ozawa, Woodland Hills, CA (US); Joonho Hyun, Valencia, CA (US); Vasily Dronov, San Jose, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/696,819

(22) Filed: Apr. 27, 2015

(65) Prior Publication Data

US 2015/0224328 A1 Aug. 13, 2015

Related U.S. Application Data

(62) Division of application No. 13/164,005, filed on Jun. 20, 2011, now Pat. No. 9,044,616.

(60) Provisional application No. 61/360,536, filed on Jul. 1, 2010.

(51) Int. Cl.
*A61N 1/372* (2006.01)
*A61N 1/378* (2006.01)
(Continued)

(52) U.S. Cl.
CPC .......... *A61N 1/37223* (2013.01); *A61N 1/3787* (2013.01); *H01Q 1/273* (2013.01); *H01Q 9/42* (2013.01)

(58) Field of Classification Search
None
See application file for complete search history.

(56) References Cited

U.S. PATENT DOCUMENTS 5,058,581 A 10/1991 Silvian
5,562,713 A 10/1996 Silvian
(Continued)

FOREIGN PATENT DOCUMENTS

JP 5-317434 12/1993
JP 2004-073725 3/2004
(Continued)

OTHER PUBLICATIONS

Tang et al., "Data Transmission from an Implantable Biotelemeter by Load—Shift Keying Using Circuit Configuration Modulator," IEEE Transactions on Biomedical Engineering. 42; 5, pp. 524-528 (1995).

*Primary Examiner* — Brian T Gedeon
(74) *Attorney, Agent, or Firm* — Lewis & Reese, PLLC

(57) ABSTRACT

A base station for passively recharging a battery in an implant without patient involvement is disclosed. The base station can be hand held or may comprise equipment configured to be placed at a fixed location, such as under a bed, on or next to a wall, etc. The base station can generate electric and magnetic fields (E-field and B-field) that couple with an antenna and a receiving coil within the implant to generate a charging current for charging the implant's battery. No handling or manipulation on part of the patient is necessary; the implant battery is passively charged whenever the patient is within range of either the magnetic or electric charging fields generated by base station. Charging using the B-field occurs when the IPG is at a relatively short distance from the base station, while charging using the E-field occurs at longer distances.

17 Claims, 12 Drawing Sheets

(51) Int. Cl.
 *H01Q 1/27* (2006.01)
 *H01Q 9/42* (2006.01)

(56) References Cited

U.S. PATENT DOCUMENTS

| | | |
|---|---|---|
| 5,733,313 A | 3/1998 | Barreras |
| 5,769,877 A | 6/1998 | Barreras |
| 6,430,444 B1 | 8/2002 | Borza |
| 7,317,946 B2 | 1/2008 | Twetan et al. |
| 7,406,349 B2 | 7/2008 | Seeberger et al. |
| 7,554,493 B1 | 6/2009 | Rahman |
| 7,729,776 B2 | 6/2010 | Von Arx et al. |
| 2004/0085247 A1 | 5/2004 | Mickle et al. |
| 2004/0098068 A1 | 5/2004 | Carbunaru et al. |
| 2007/0191908 A1 | 8/2007 | Jacob et al. |
| 2008/0027500 A1 | 1/2008 | Chen |
| 2008/0097554 A1 | 4/2008 | Payne et al. |
| 2008/0172109 A1 | 7/2008 | Rahman et al. |
| 2009/0024179 A1 | 1/2009 | Dronov |
| 2009/0069869 A1 | 3/2009 | Stouffer et al. |
| 2009/0192575 A1 | 7/2009 | Carbunaru et al. |
| 2009/0222066 A1 | 9/2009 | Chen et al. |
| 2009/0281597 A1 | 11/2009 | Parramon et al. |
| 2009/0306738 A1 | 12/2009 | Weiss et al. |
| 2010/0161002 A1 | 6/2010 | Aghassian et al. |
| 2011/0004278 A1 | 1/2011 | Aghassian et al. |
| 2011/0093048 A1 | 4/2011 | Aghassian |
| 2011/0112610 A1 | 5/2011 | Rahman et al. |
| 2011/0112611 A1 | 5/2011 | Aghassian |
| 2013/0018438 A1 | 1/2013 | Chow et al. |
| 2013/0018440 A1 | 1/2013 | Chow et al. |

FOREIGN PATENT DOCUMENTS

| | | |
|---|---|---|
| WO | 00/13585 | 3/2000 |
| WO | 2007/098367 | 8/2007 |

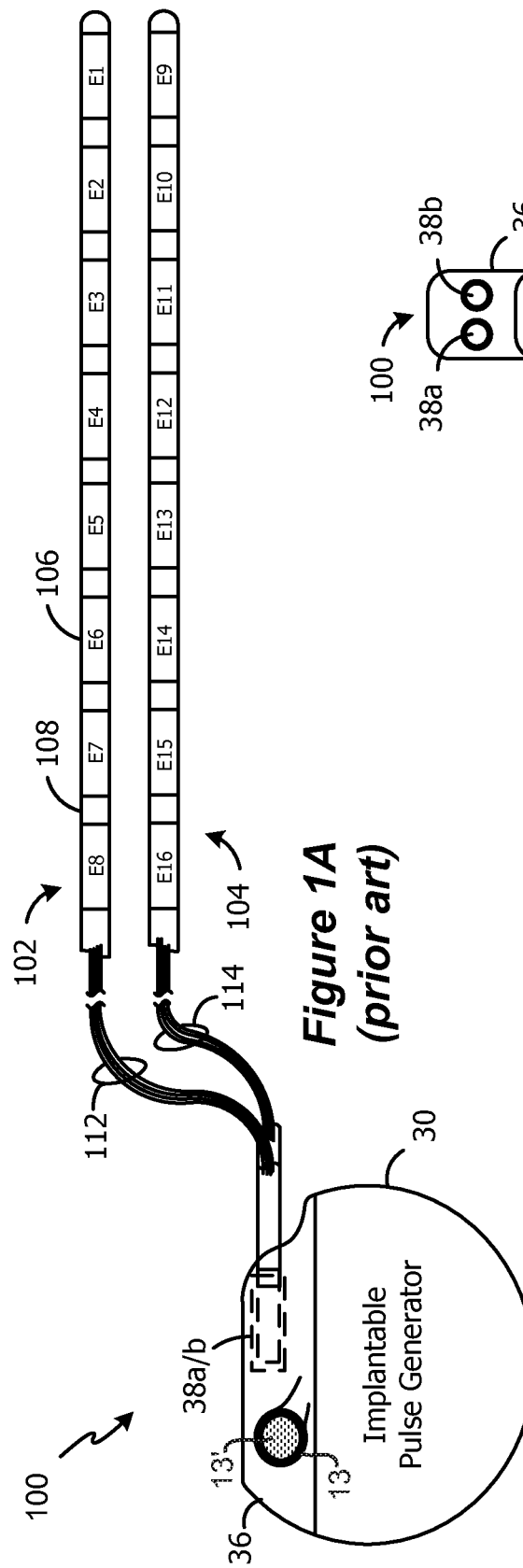
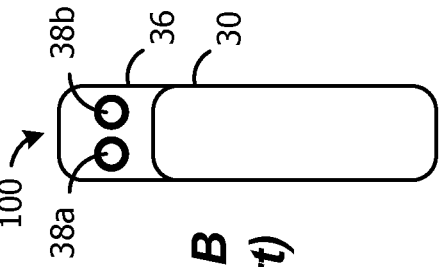
Figure 1A (prior art)
Figure 1B (prior art)

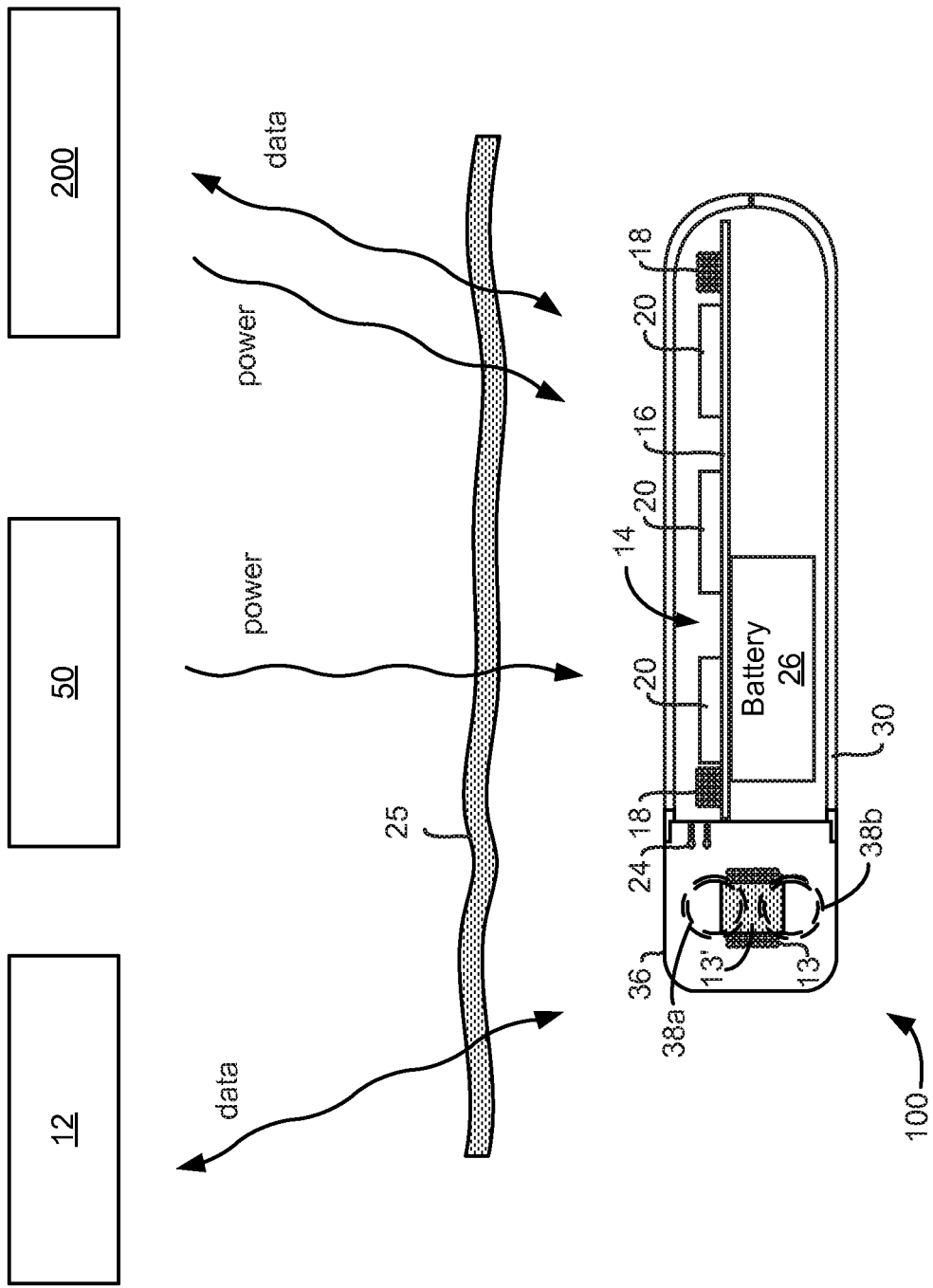

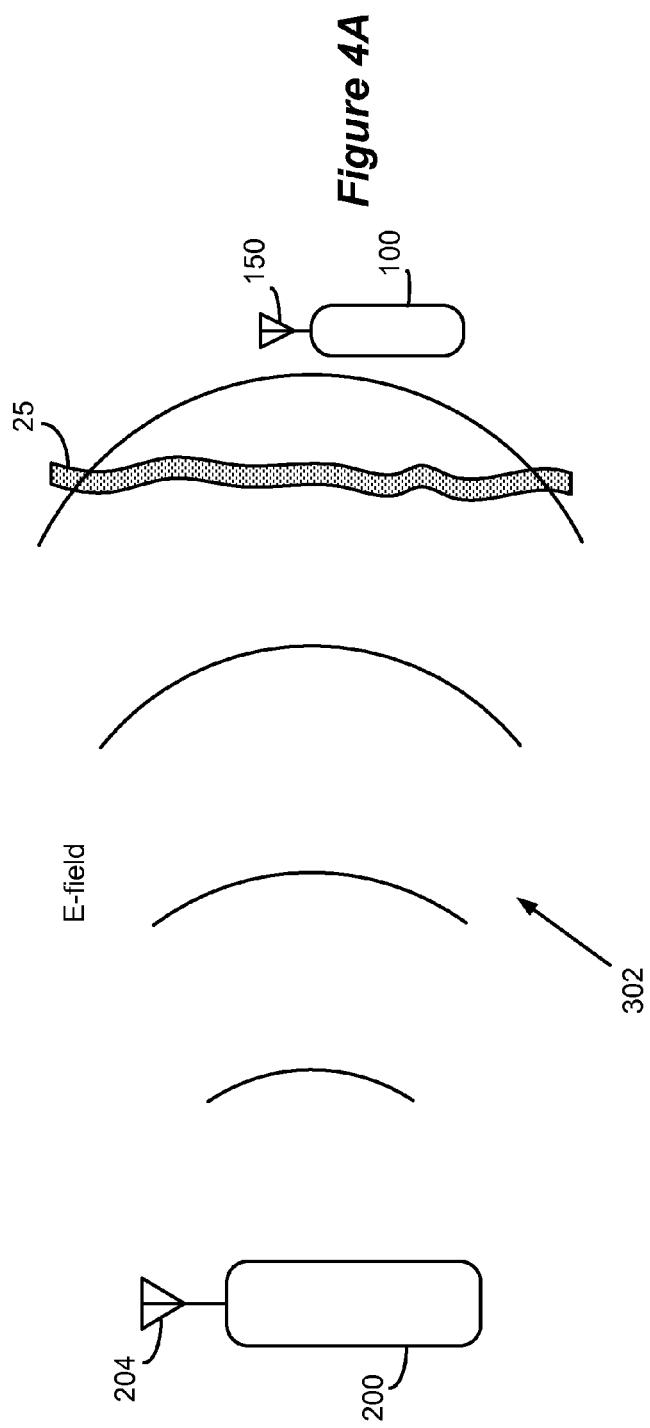
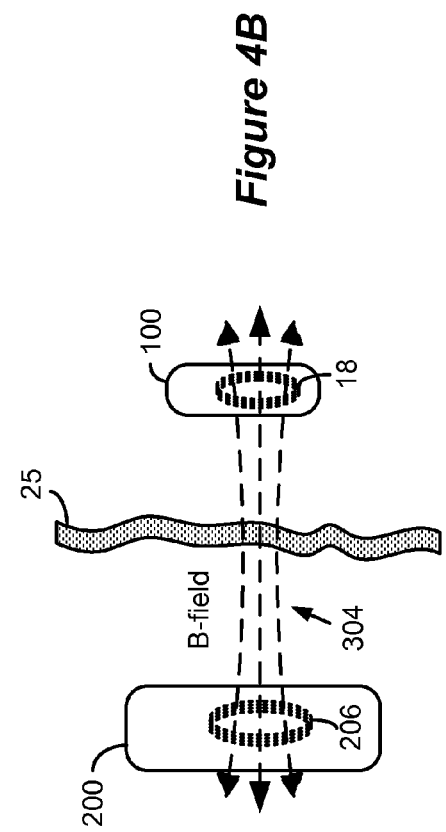

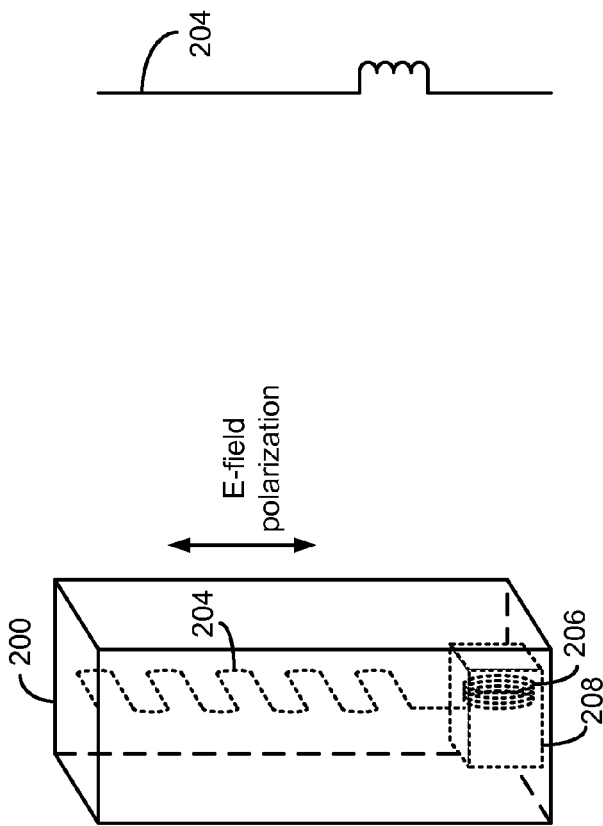
*Figure 5A*
*Figure 5B*
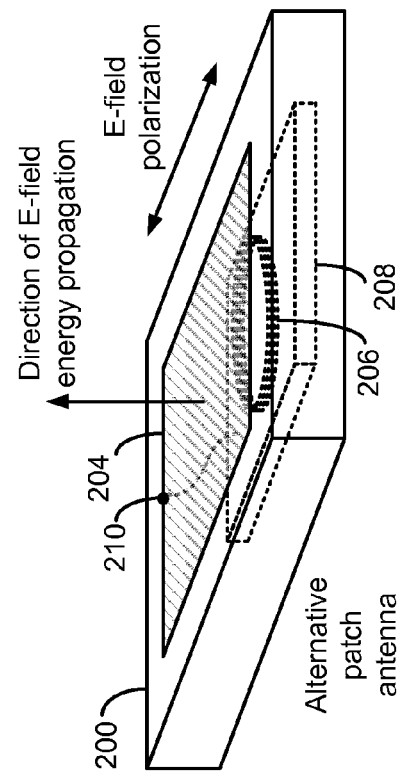
*Figure 5C*

CHARGING SYSTEM FOR AN IMPLANTABLE MEDICAL DEVICE EMPLOYING MAGNETIC AND ELECTRIC FIELDS

CROSS REFERENCE TO RELATED APPLICATIONS

This is a divisional application of U.S. patent application Ser. No. 13/164,005, filed Jun. 20, 2011, which is a non-provisional application of U.S. Patent Application Ser. No. 61/360,536, filed Jul. 1, 2010. Priority is claimed to these applications, and they are incorporated herein by reference in their entireties.

FIELD OF THE INVENTION

The present invention relates to improved battery charging for an implantable medical device.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are eight electrodes on array 102, labeled $E_1$-$E_8$, and eight electrodes on array 104, labeled $E_9$-$E_{16}$, although the number of arrays and electrodes is application specific and therefore can vary. The arrays 102, 104 couple to the IPG 100 using lead connectors 38a and 38b, which are fixed in a non-conductive header 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transmit/receive data to/from an external controller 12; and a charging coil 18 for charging or recharging the IPG's battery 26 using an external charger 50. The telemetry coil 13 is typically mounted within the header 36 of the IPG 100 as shown, and may be wrapped around a ferrite core 13'.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

The external charger 50, also typically a hand-held device, is used to wirelessly convey power to the IPG 100, which power can be used to recharge the IPG's battery 26. The transfer of power from the external charger 50 is enabled by a coil (antenna) 17'. For the purpose of the basic explanation here, the external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via inductive coupling, and specifically magnetic inductive coupling. To implement such functionality, both the IPG 100 and the external devices 12 and 50 have coils which act together as a pair. In case of the external controller 12, the relevant pair of coils comprises coil 17 from the controller and coil 13 from the IPG 100. In case of the external charger 50, the relevant pair of coils comprises coil 17' from the charger and coil 18 from the IPG 100.

When data is to be sent from the external controller 12 to the IPG 100 for example, coil 17 is energized with an alternating current (AC). Such energizing of the coil 17 to transfer data can occur using a Frequency Shift Keying (FSK) protocol for example, such as disclosed in U.S. Patent Application Publication 2009/0024179. Energizing the coil 17 produces a magnetic field, which in turn induces a voltage in the IPG's coil 13, which produces a corresponding current signal when provided a closed loop path. This voltage and/or current signal can then be demodulated to recover the original data. Transmitting data from the IPG 100 to the external controller 12 occurs in essentially the same manner.

When power is to be transmitted from the external charger 50 to the IPG 100, coil 17' is again energized with an alternating current. Such energizing is generally of a constant frequency, and may be of a larger magnitude than that used during the transfer of data, but otherwise the basic physics involved are similar.

The IPG 100 can also communicate data back to the external charger 50 by modulating the impedance of the charging coil 18. This change in impedance is reflected back to coil 17' in the external charger 50, which demodulates the reflection to recover the transmitted data. This means of transmitting data from the IPG 100 to the external charger 50 is known as Load Shift Keying (LSK), and is useful to communicate data relevant during charging of the battery 26 in the IPG 100, such as the capacity of the battery, whether charging is complete and the external charger can cease, and other pertinent charging variables. LSK communication from an IPG 100 to an external charger is discussed further in U.S. Patent Application Publication 2010/0179618.

As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

Although the burden on the patient to charge the IPG seems minimal, the inventors recognize that some percentage of the patient population does not have the skills necessary to operate the charger 50. For example, some patients may be physically impaired and thus unable to place a charger 50 at the appropriate location over the IPG 100. Furthermore, even in patients that are able, it may be difficult for the patient to tell where the IPG 100 is located, or what an appropriate alignment would be between the charger 50 and the IPG 100. In short, the need for the patient's involvement in the charging process can be problematic, and the inventors here introduce a solution that can allow patients to recharge their implants with no or little participation.

BRIEF DESCRIPTION OF THE DRAWINGS

FIGS. 1A and 1B show an implantable medical device, and the manner in which an electrode array is coupled to the IPG in accordance with the prior art.

FIG. 3 shows the addition of a base station charger to the system of FIG. 2.

FIGS. 4A and 4B show the base station charging an IPG using an E-field and a B-field, respectively, in accordance with an embodiment of the invention.

FIGS. 5A-5E depict various physical embodiments of base station of FIG. 3.

DETAILED DESCRIPTION

Figure 2:
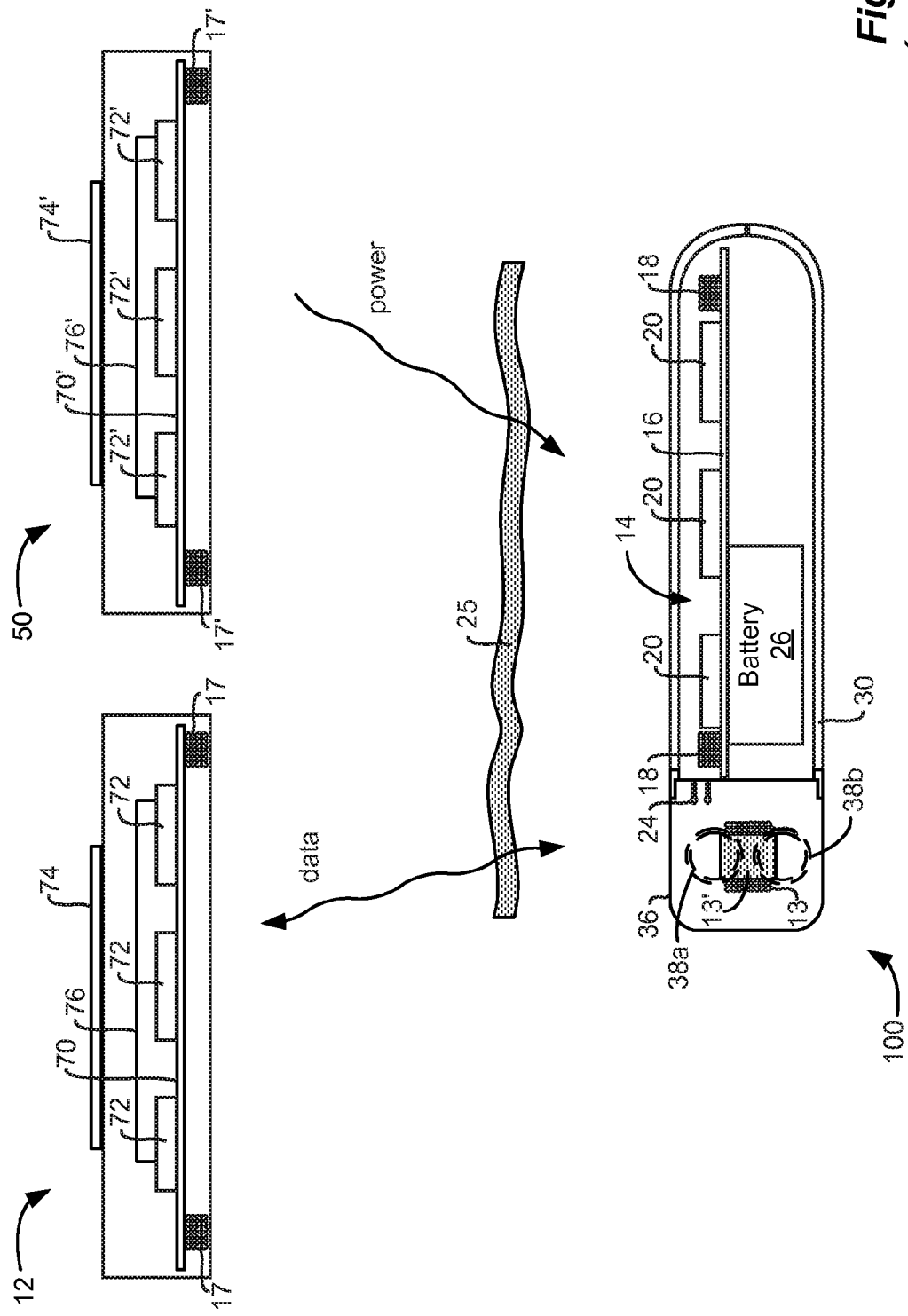
FIG. 2 shows the relation between the implantable medical device, an external controller, and an external charger.

The description that follows relates to use of the invention within spinal cord stimulation (SCS) system. However, it is to be understood that the invention is not so limited, and could be used with any type of implantable medical device system.

The inventors address the problem of recharging a battery in an implant by providing a external device that can passively recharge the battery without patient involvement. The external device is referred to as a base station 200, and is shown in conjunction with a traditional external controller 12 and external charger 50 in FIG. 3. The base station 200 can be hand held similar to devices 12 or 50, but in the disclosed embodiments is described as equipment configured to be placed at a fixed location, such as under a bed, on or next to a wall, etc. In other words, the base station 200 would normally be located somewhere where the patient would be expected to spend a significant amount of time—time which can be spent recharging the battery. The base station 200 could be battery-powered, but would more likely be plugged into a wall socket.

Base station 200 in one embodiment can generate an electric field and a magnetic field (E-field and B-field) that couple with an antenna and a receiving coil within the IPG 100 to generate a charging current for charging the IPG battery 26. No handling or manipulation on part of the patient is necessary; the implant battery is passively charged whenever the patient is within range of either the magnetic or electric charging fields generated by base station 200. Charging using the B-field occurs when the IPG is at a relatively short distance from the base station 300 (e.g., less than 1 m), while charging using the E-field occurs at longer distances (e.g., >1 m). Back telemetry from the IPG 100 to the base station 200 can be used to inform the base station 200 as to whether charging should occur via B-field or E-field, and B-field charging is preferred if possible for its ability to transfer higher amounts of power to the IPG 100, as will be explained here.

FIGS. 4A and 4B illustrate both E-field and B-field modes of operation of the base station 300. FIG. 4A shows base station 200 using an antenna 204 for generating a radiating E-field 302. The E-field 302 is sensed by an antenna 150 in IPG 100 to generate an alternating current, which is rectified to produce DC power to recharge the battery, as will be described in further detail later. Because these antennas 204 and 150 primarily interact with the electrical component of the electromagnetic field, FIG. 4A illustrates only the E-field 302. FIG. 4B shows the base station 200 using a coil (antenna) 206 for generating an inductive B-field 304. Coil 18 in IPG 100 couples with the B-field 304 to generate an alternating current, which is rectified to produce DC power. Such B-field charging is similar to the charging scheme implemented in a traditional external charger 50 (FIG. 2), and uses similar circuitry, although circuitry in the base station 302 has been modified as discussed herein. For example, the base station's circuitry allows for selection of the charging mode—E-field 302 or B-field 304—to transfer energy to the IPG 100. As discussed further below, the B-field 304 is typical a lower frequency (e.g., on the order of 100 kHz) than the E-field 302 (e.g., on the order of 1 MHz to 10 GHz).

As noted, and as depicted in FIG. 4, E-field charging will be used for longer distances, while B-field charging will be used for shorter distances. The strength of an E-field, such as E-field 302, typically reduces proportional to the square of the distance between the transmitting antenna 204 and the receiving antenna 150. In contrast, strength of an inductive magnetic field, such as B-field 304, typically reduces proportional to the cube of the distance between the generating coil 206 and the receiving coil 18. Therefore, for larger distances, transferring energy using an E-field is more efficient that using a B-field.

Figure 5D:
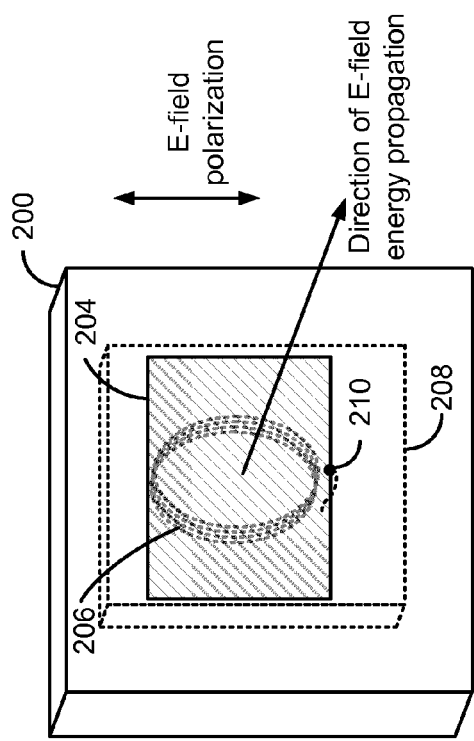

Before discussing the circuitry and operation of the base station 200, various physical embodiments of base station 200 are discussed, as shown in FIGS. 5A-5E. As noted earlier, base station 200 can be positioned on a wall or floor, i.e., placed near a bed, against a wall, in a corner, or at any other convenient location generally close to an expected location of a patient. FIG. 5A shows base station 200 having a serpentine wire antenna 204 connected to a circuit module 208. As will be discussed later, circuit module 208 includes circuitry such as microcontrollers, amplifiers, transceivers, etc., for operating base station 200. Serpentine antenna 204 is energized by the circuit module 208 for radiating the E-field 302. Alternatively, an inductively-loaded antenna such as the one shown in FIG. 5B can be used in place of the serpentine antenna. Generally, both the antennas 204 illustrated in FIGS. 5A and 5B would be quarter-wavelength monopole antennas. A quarter-wavelength antenna ideally has a length equal to one-fourth of the wavelength of the E-field being radiated. For example, a quarter-wavelength antenna 204 of length 0.25 m would be used for transmitting a wavelength of 1 meter (which corresponds to a frequency of approximately 300 MHz). Because of the serpentine shape of the antenna of FIG. 5A, and because of the inductive loading of the antenna of FIG. 5B, these antennas can be made smaller than the optimal quarter-wavelength length. Base station 200 can be equipped with a parabolic reflector (not shown) placed behind the antenna 204 to radiate or propagate energy of the E-field in the desired direction. This can be of particular advantage to focusing the radiating E-field towards the patient's IPG 100.

Base station 200 also includes the coil 206 for generating the B-field 304, which coil is also coupled to the circuit module 208. Coil 206 is typically wound on a ferrite core (not shown) to increase the strength of produced inductive field.

Because the antennas 204 of FIGS. 5A and 5B are vertically oriented, the electromagnetic wave radiated from the antenna 204 is also vertically oriented, i.e., vertically polarized. If the IPG antenna 150 is also vertically oriented, maximum coupling with the vertically oriented E-field 302 will occur. Maximum coupling is favorable because it results in the maximum E-field power transfer, thus providing more energy to recharge the IPG 100's battery 26. Such coupling will diminish as the angle between the polarization of the E-field 302 and the orientation of the receiving IPG antenna 150 increases, with minimum coupling at a 90-degree angle.

FIG. 5C shows another embodiment of a base station 200 that includes a patch antenna 204 coupled to the circuit module 208. Patch antenna 204 is typically made of a square or rectangular metal plate placed at a certain distance over a ground plane, which may comprise an additional metal plate connected to ground or the floor itself. Patch antennas generally operate as dipole, or half-wavelength antennas, meaning that the antenna is ideally dimensioned to half the wavelength of the transmitted electromagnetic wave. For example, if the patch antenna 204 is used to generate an E-field 304 at 300 MHz, the length of patch antenna would ideally be equal to 0.5 m. Patch antenna 204 of FIG. 5C will radiate or propagate energy of an E-field vertically upwards, i.e., in a direction that is generally normal to the plane of the patch antenna, and is therefore useful for placement underneath a patient's bed for example to allow for IPG charging while the patient is sleeping. Polarization of the E-field generated by the patch antenna is determined by the location of the contact(s) 210 as shown in FIG. 5C, which is the location where the patch antenna is coupled to the circuit module 208. Again, maximum coupling between the E-field generated by the patch antenna 204 and the IPG antenna 150 will occur when the direction of the IPG antenna 150 is the same as the direction of the polarization of the E-field. Note that the base station of FIG. 5C can also be placed vertically, as shown in FIG. 5D. Such orientation could be mounted on a wall, and might be more advantageous to recharge an IPG in a patient sitting in a nearby chair for example. Antenna 204 can also comprise a slot antenna.

Figure 5E:
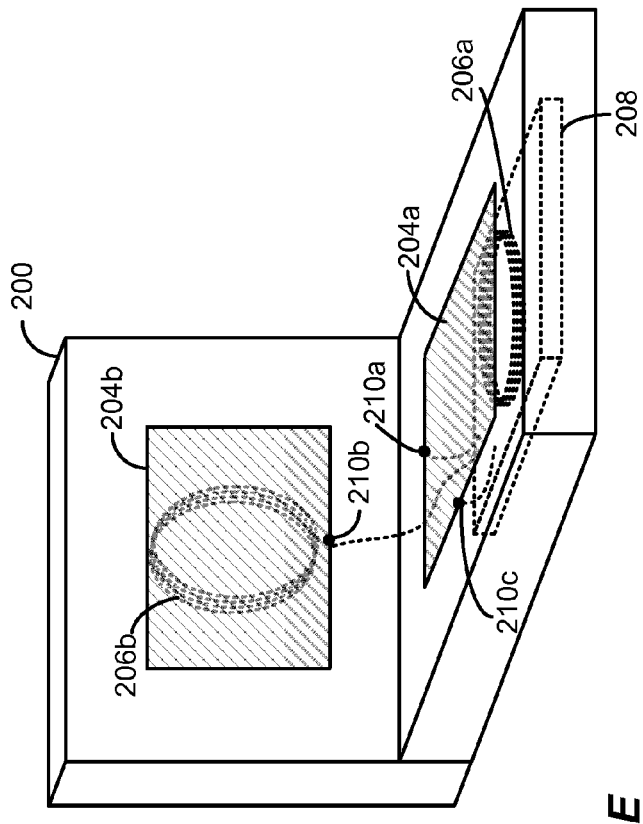

FIG. 5E shows an embodiment of base station 200 that combines the embodiments shown in FIGS. 5C and 5D, and thus provides both horizontal and vertical polarization of the produced E-field. Because the produced E-field is polarized in two directions, it will more likely couple to the antenna 150 in the IPG 100, which antenna 150 orientation may not be known exactly or can vary as the patient moves. In this embodiment, the base station 200 includes two patch antennas 204a and 204b respectively placed in horizontal and vertical planes, allowing the energy of E-field to be radiated or propagated in both upward and sideways directions. Patch antenna 204a also includes two contact points 210a and 210c, which allows the base station 200 to select the desired polarization. Patch antenna 204a can be simultaneously energized at both contact points 210a and 210c to generate a circularly-polarized E-field, typically by energizing points 210a and 210c 90-degrees out of phase. Such circularly polarized field minimizes constraints on the orientation of the IPG antenna 150 for maximum coupling. Patch antenna 204b may likewise contain two contact points and produce a circularly-polarized E-field, although this is not shown in FIG. 5E for clarity.

The base station 200 of FIG. 5E also contains two cols 206a and 206b. Like the antennas 204a and 204b, the coils 206a and 206b are orthogonal, and produce B-fields which are orthogonal, which minimizes constraints on the orientation of the IPG coil 18 (FIG. 4B). A rotating B-field can also be produced using the two coils 206a and 206b. See, e.g., U.S. Patent Application Publication 2009/0069869, which is incorporated herein by reference in its entirety.

Base station 200 can also select the antenna 204a or 204b, or coil 206a or 206b, that provides maximum power transfer to the IPG 100, and use only that antenna or coil. This selection can be based on assessing coupling information for each antenna and coil orientation, which information can be telemetered from the IPG 100, or can be deduced based on the production of the E-field or B-field at the base station 200. See, e.g., U.S. Patent Application Publication 2008/0172109, which is incorporated herein by reference.

Figure 6:
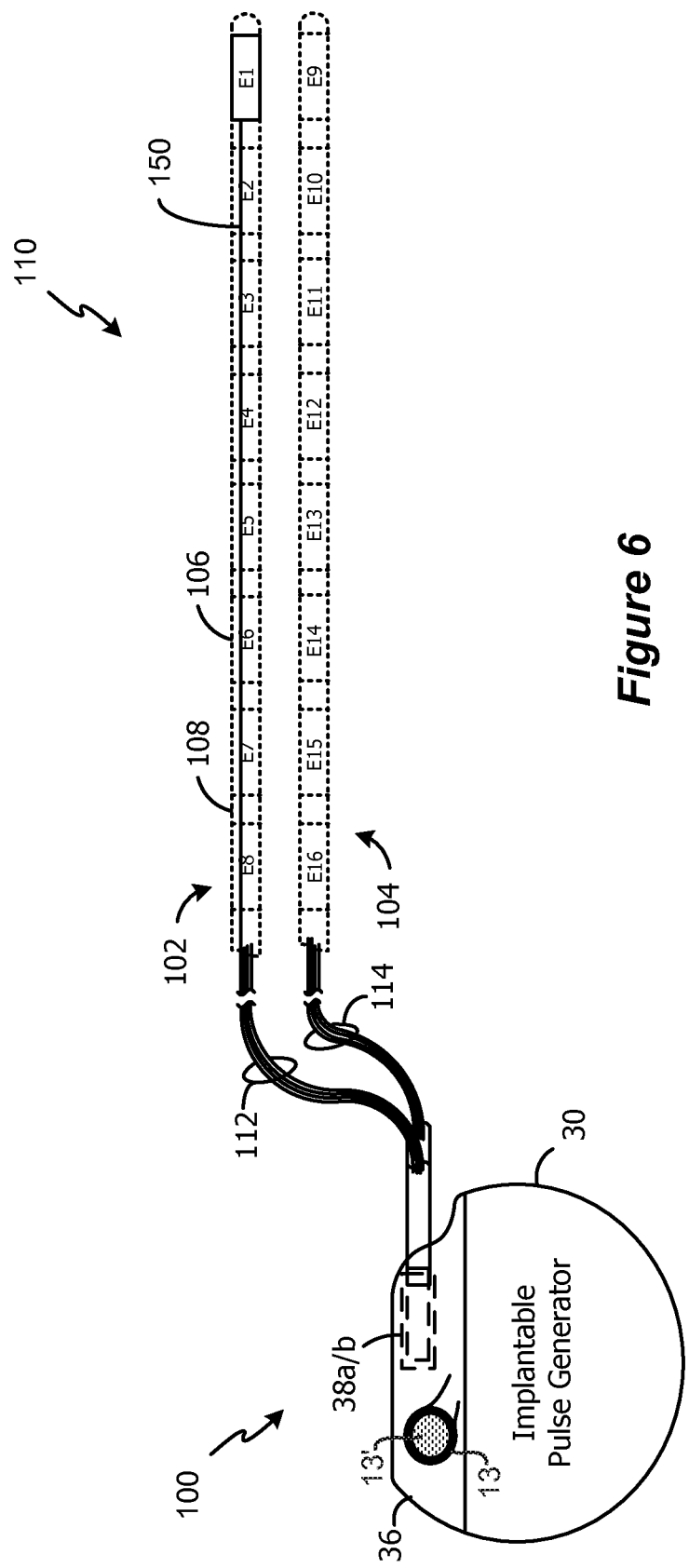
FIG. 6 shows an IPG electrode being used as an antenna for E-field reception in accordance with an embodiment of the invention.

FIG. 6 shows further details of a suitable E-field antenna 150, and in this embodiment antenna 150 comprises one of the electrode leads 112 used in array 102 as the antenna 150. For example, the wire connecting to electrode $E_1$ is used as the antenna 150. Wires to other electrodes (E2, E3) can also be used, but because selecting the longest wire advantageously reduces the transmission frequency, the wire to electrode $E_1$ has been chosen. (Of course, a signal wire connecting to electrodes on array 104 can also be chosen). Because electrode leads 112 and 114 provide individual wires of varying lengths, a wire whose length is closest to the ideal length for a particular E-field receiving/transmitting frequency can be readily selected. Note that using an electrode lead for the antenna 150 does not affect stimulation produced at the affected electrode because the frequency of the E-field 302 received or transmitted by antenna 150 is at least a few orders of magnitude higher than the frequency of signals sent to electrodes. For example, the E-field 302 is typically on the order of 1 MHz to 10 GHz, while the frequencies of pulses sent to the electrode via a signal wire are in the range of tens of Hz to hundreds of Hz. Moreover, the magnitude of the AC signal on the signal wire resulting from E-field transmission or reception is typical very small (e.g., mV) compared to the magnitude of the stimulation pulses (e.g., Volts). Of course, the IPG 100 can also include a dedicated antenna, separate from the electrode leads 112 and 114, for transmitting and receiving the E-field 302 to and from the base station 200. Such an antenna can be placed in the header 36 or in the metal case 30 of the IPG 100.

Figure 7:
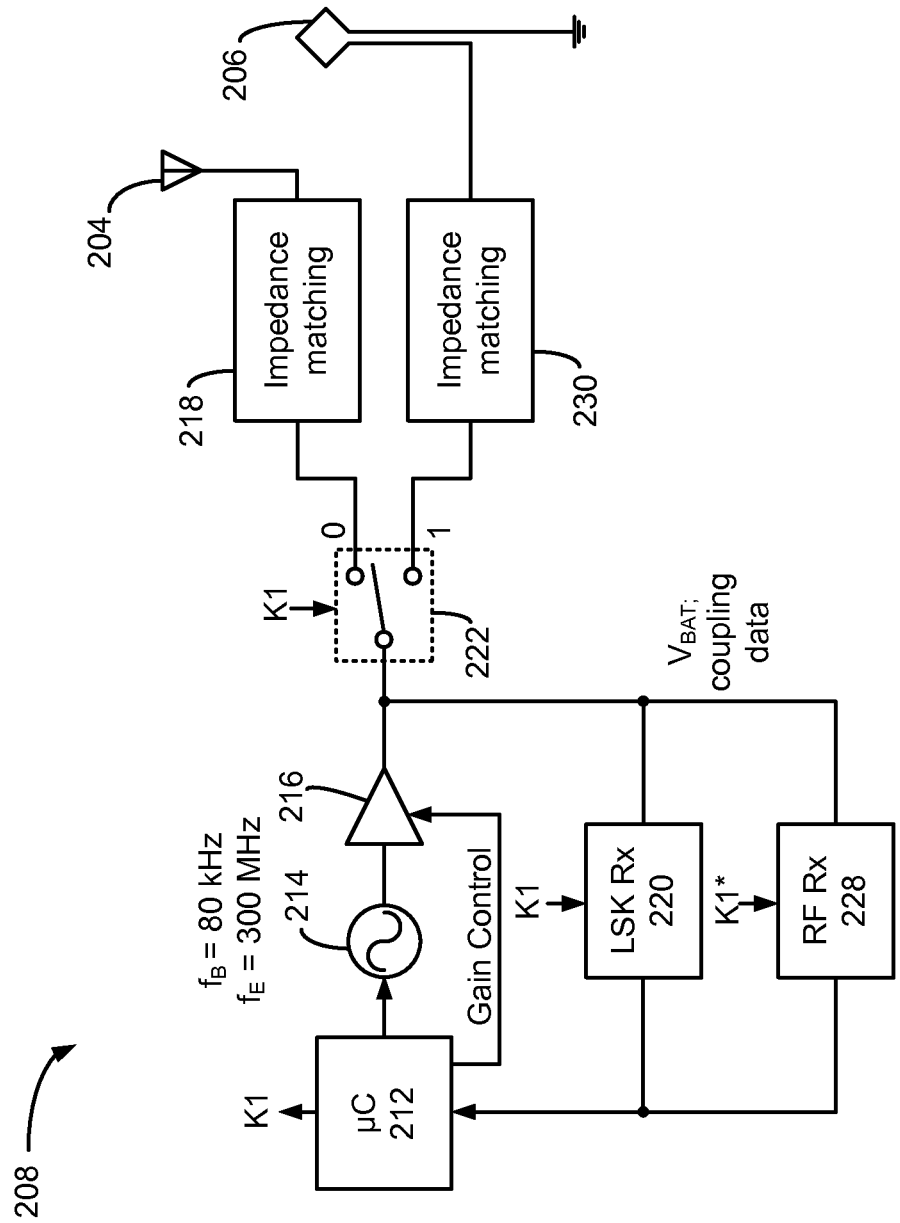
FIG. 7 shows a schematic of the circuitry within the base station in accordance with an embodiment of the invention.

Discussion now turns to the circuit module 208 in the base station 200 used to transfer and receive energy to and from the IPG 100. As shown in FIG. 7, microcontroller 212 controls the operation of the transmission circuitry and receiver circuitry, as well as controlling other operations in the base station 200 not discussed here. As is typical, microcontroller 212 can include both volatile memory (e.g., RAM) and non-volatile memory (e.g., Flash, EEPROM) for storing and implementing the functionality described herein. Transmission circuitry includes a digitally-controlled signal generator 214 and power amplifier 216. Receiver circuitry includes two receiver circuits, LSK Rx 220 and RF Rx 228. Switch 222 couples the transmission and receiver circuitry to either the antenna 204 or the coil 206, depending on whether E-field or B-field charging has been selected.

For transferring energy using coil 206 via B-field 304, microcontroller 212 controls the signal generator 214 to generate a signal with a transmission frequency of $f_B$=80 kHz for example. Signal generator 214 will typically generate a sinusoidal signal at the specified frequency, but can also generate waveforms with a varying duty-cycle.

For transferring energy using antenna 204 via E-field 302, microcontroller 212 controls the signal generator to generate a signal with a transmission frequency of $f_E$. $f_E$ can range from about 1 MHz to 10 GHz, and whether higher or lower frequencies are used for $f_E$ involve tradeoffs. Transmitting at higher frequencies allows higher energy to be transmitted to the IPG 200, and at longer distances. However, high frequency signals are attenuated by the body tissue. Lower frequencies have less attenuation, but can require a longer antenna 150 in the IPG 100 for optimal quarter-wavelength tuning Antenna length is mitigated slightly by the permittivity of the tissue, which is primarily water. Because the length of the antenna 150 will scale in inverse proportion to the square root of the permittivity of the tissue (water), the required length of the antenna 150 can be shortened significantly, which will allow $f_E$ to be lowered. In any event, a lack of precise tuning and the reality of signal attenuation can be mitigated by proper antenna circuitry design and by adjusting the power of the E-field transmission, and it is not strictly necessary that an antenna 150 in the IPG 100 be exactly one-quarter of the wavelength of $f_E$. In useful embodiments, $f_E$ can comprise a frequency selected from the Industrial, Scientific, and Medical (ISM) band in one example, and could comprise frequencies of 13.56 MHz, or 27.12 MHz, or 2.45 GHz for example, even if the antenna 150 in the IPG 100 is not dimensioned to resonate optimally at such frequencies.

The output of signal generator 214 is fed to the input of power amplifier 216, which amplifies its input signal by a magnitude controlled by the microcontroller 212 using a gain control signal. In reality, separate amplifiers 216 may be used depending on the frequency ($f_E$ or $f_B$) chosen, but this is not shown in FIG. 7 for simplicity. Initially, the microcontroller 212 may set a default gain for power amplifier 216 via the gain control signal, which signal can be increased as necessary.

The output of the power amplifier 216 is ultimately sent to either of antennas 204 or coil 206 via appropriate impedance matching circuitry 218 and 230. Impedance matching circuits are well known in the art, and can include transformers, passive RLC networks, stepped transmission lines, etc. Which of the antenna 204 or coil 206 are chosen is determined by a control signal K1 issued from the microcontroller 212, which equals a logic '1' when B-field charging is used, and a logic '0' when E-field charging is used. When K1=1, switch 222 couples the transmission and receiver circuitry to coil 206 via its impedance matching circuitry 230. When K1=0, switch 222 couples the circuitry to antenna 204 via its impedance matching circuitry.

In the embodiment of FIG. 7, base station 200 includes two receiver circuits for receiving back-telemetry data from the IPG 100 during recharging of the IPG battery 26. LSK receiver 220 receives load-shift-keyed data via coil 206, while RF receiver 228 receives modulated data via antenna 204. Like switch 222, these receivers 220 and 228 are controlled by K1, such that only one of them is enabled at a time, depending on whether the base station is operating in B-field or E-field mode. LSK telemetry is well known, and involves modulating the resistance of the receiving coil 18 in the IPG to produce detectable reflections at the transmitting coil 206, as is explained further below with reference to FIG. 8A.

Charging information back telemetered from the IPG 100 can include the IPG's battery voltage ($V_{BAT}$) and data indicative of the coupling between the base station and the IPG. $V_{BAT}$ informs the microcontroller 212 of the present voltage of the IPG battery 26 during charging to allow the microcontroller 212 to either modify the power of the antenna 204 or coil 206 broadcasting the charging energy, or to suspend charging altogether once the battery 26 is full.

Figure 8A:
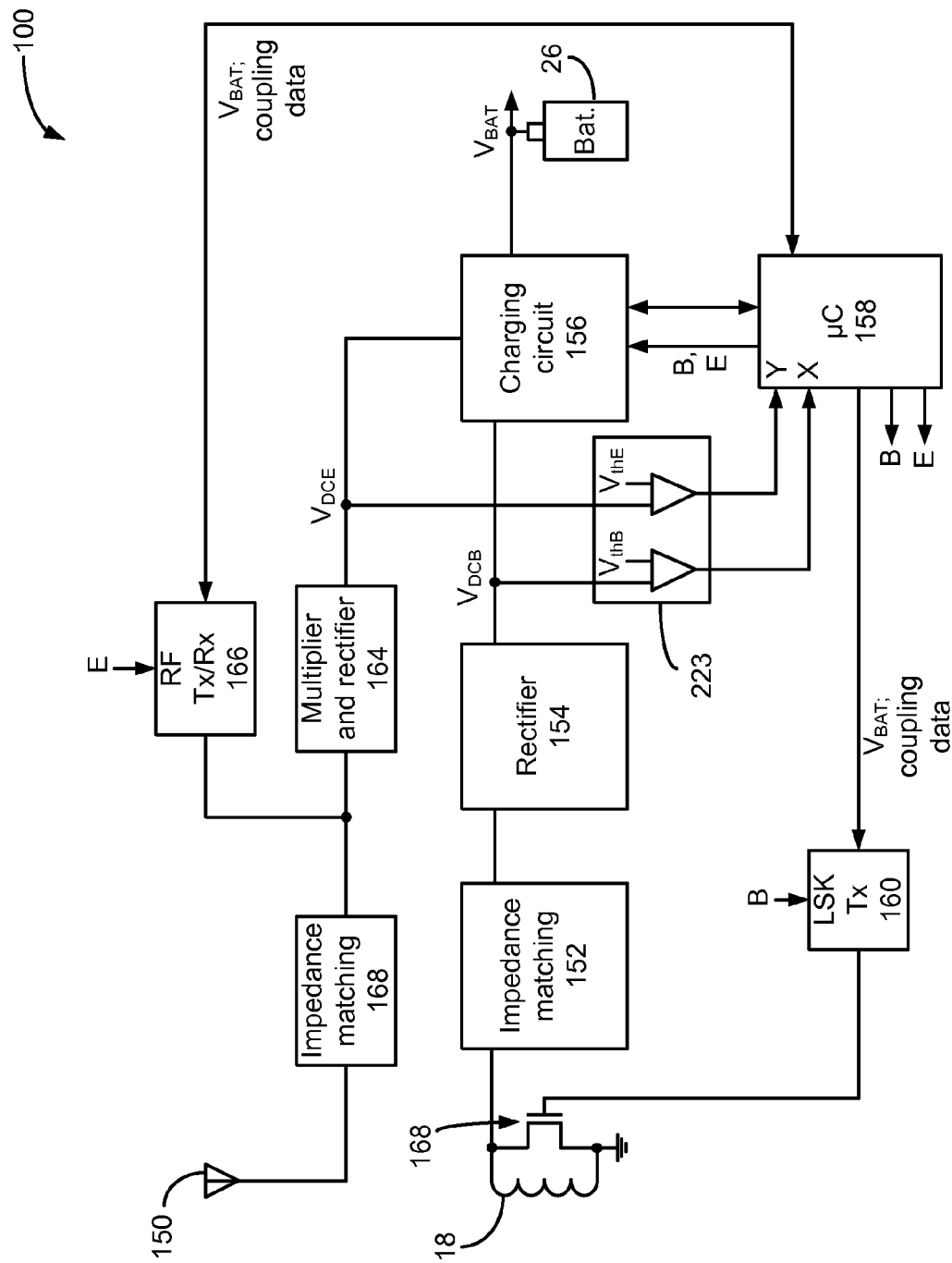
FIGS. 8A and 8B show schematics of the circuitry within the IPG for interfacing with the base station in accordance with an embodiment of the invention.

Coupling data received from the IPG 100 indicates the amount of energy that the IPG is receiving, and will depend upon several factors, such as transmission power, distance between the base station 200 and the IPG 100, relative orientations of the transmitting/receiving elements (antenna 204 and antenna 150; or coil 206 and 18), etc. In one embodiment, coupling data can comprise the voltages $V_{DCE}$ and $V_{DCB}$ respectively output by the B-field and E-field rectifiers 154 and 164 in the IPG 100, as will be discussed later with reference to FIG. 8A. In another embodiment, coupling data can comprise a voltage drop across charging circuitry 156 (FIG. 8A). See, e.g., U.S. Pat. No. 8,744,592, which is incorporated herein by reference in its entirety. When the base station 200 receives such coupling data during charging, it can control the gain of power amplifier 216 via the gain control signal. For example, if the output voltage of rectifiers 154 or 164 (FIG. 8A), $V_{DCE}$ or $V_{DCB}$, in the IPG 100 reduces below a predetermined value, microcontroller 212 can increase the gain of power amplifier 216 so that the magnitude of the produced E-field 302 or B-field 304 increases. How to adjust the gain control signal for a particular received value of the coupling data can be determined by experimentation or simulation, and can be stored as a look up table in memory associated with the microprocessor 212.

Figure 8B:
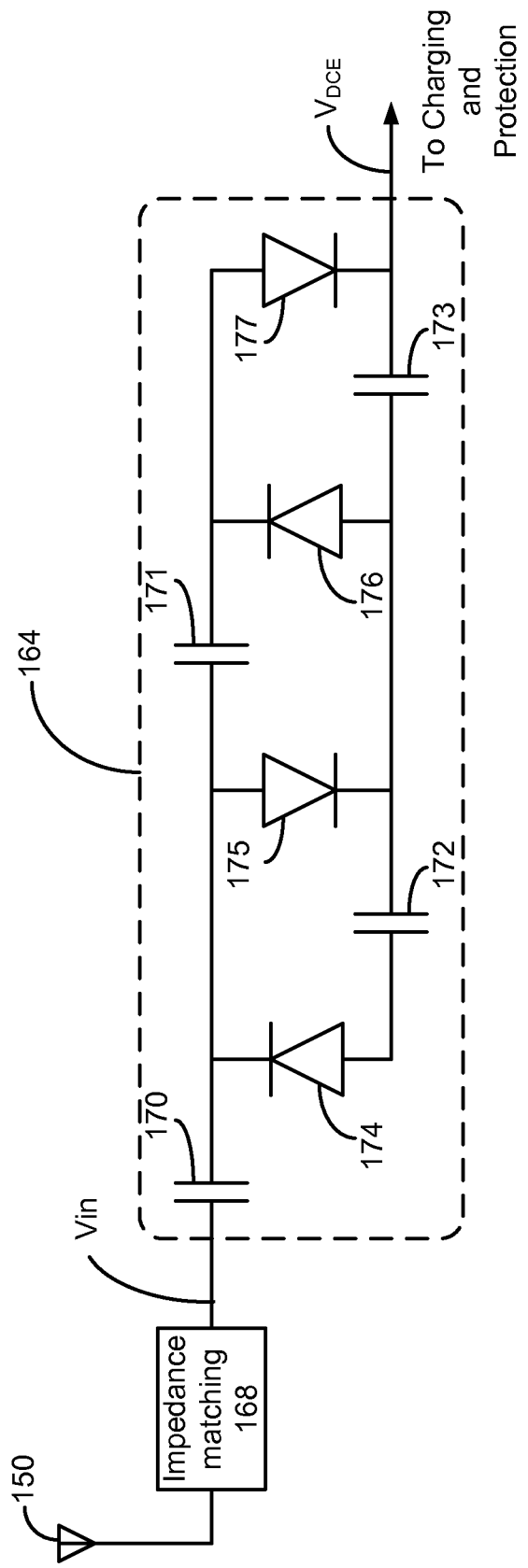

FIG. 8A shows an embodiment of the circuitry in the IPG 100 for receiving the charging energy broadcast by the base station 200, and for back telemetering charging information to the base station 200. Antenna 150, which again can comprise one of the signal wires as discussed earlier with respect to FIG. 6, is coupled to a multiplier and rectifier 164 through an impedance matching circuit 168, and receives the E-field 302 generated by the base station 200. The rectifier 164 generates a DC voltage, $V_{DCE}$, which is used to charge the battery 26. FIG. 8B illustrates an example circuit that can be used for rectifier 164, which is known in the art as a half-wave series multiplier or a Villard cascade. The rectifier 164 comprises a number of capacitor-diode stages, with four such stages shown in FIG. 8B. The number of stages dictates the multiplier that will be applied to the AC input voltage, Vin, to produce DC voltage $V_{DCE}$, such that four stages will essentially produce a $V_{DCE}$ that is four times the peak voltage of Vin. Diodes 174-177 are preferably zero threshold or low threshold diodes such as Schottky diodes, which will allow for the rectification and multiplication of small AC voltage, Vin, produced at the output of the antenna 150 (tens to hundreds of mVs). $V_{DCE}$ is fed to the charging circuit 156, which monitors and controls the battery's 26 charging process.

Referring again to FIG. 8A, IPG 100 also includes a charging coil 18 connected to a rectifier 154 via an impedance matching circuit 152. This coil 18 receives the B-field 304 generated by the base station 200. Coil 18 may also receive a B-field from a more traditional external charger 50, such as was discussed in FIG. 2, and in this regard, the improved circuitry of FIG. 8A does not disrupt the use of such legacy system designs. Impedance matching circuit 152 matches the impedance of the coil 18 with the input impedance of the rectifier 154 to allow for maximum power transfer. Rectifier 154 can be a single diode half-wave rectifier, a full-wave bridge rectifier, or other rectifiers well known in the art. Because the AC voltages induced on the coil 18 by the B-field are generally quite large (on the order of Volts), the rectifier can use traditional diodes. Output of the rectifier 154, $V_{DCB}$, is fed to the charging circuit 156.

Both $V_{DCE}$ and $V_{DCB}$ are fed to a comparison circuit 223 to be compared to threshold voltages $V_{thE}$ and $V_{thB}$, respectively. Generally speaking, comparison circuit 223 informs the microcontroller 158 when charging energy is being received either at the antenna 150 (via E-field charging) or at the coil 18 (via B-field charging). As shown, comparison circuit 223 can include two comparators for comparing the DC voltages produced by each of the rectifiers 164 and 154, $V_{DCE}$ and $V_{DCB}$, to reference voltages $V_{thE}$ and $V_{thB}$. If either DC voltage exceeds its associated reference voltage, its comparator will digitally indicate that fact to the IPG 100's microcontroller 158 as a logic '1' at inputs X and Y. $V_{thE}$ and $V_{thB}$ can be experimentally determined, and can be made adjustable, but in any case are generally set to a significant level to discern true power reception from mere noise. Note that because $V_{DCE}$ will often be much less than $V_{DCB}$, reference voltage $V_{thE}$ will likewise generally be much smaller than $V_{thB}$. In an alternative arrangement, if the microcontroller 158 includes or is associated with analog-to-digital converters, then $V_{DCE}$ and $V_{DCB}$ can be directly fed to such analog inputs, allowing the microprocessor 158 to assess the magnitude of those voltages digitally.

Microcontroller 158 can interpret input signals X and Y and issue control signals B and E accordingly, which control signals indicate to the remainder of the circuitry whether the microcontroller 158 is recognizing and allowing charging of the battery 26 to occur via B-field or E-field reception. The following truth table shows the generation of these control signals B and E based on input signals X and Y, and shows the preference of the IPG 100 to charge via B-field reception if that route is available.

| X | Y | B | E |
|---|---|---|---|
| 0 | 0 | 0 | 0 |
| 0 | 1 | 0 | 1 |
| 1 | 0 | 1 | 0 |
| 1 | 1 | 1 | 0 |

Allowing B-field charging to take precedence over E-field charging (i.e., B=1 when X is asserted, regardless of Y) is preferred because the rectified voltage produced via B-field reception, $V_{DCB}$, would generally be much greater than the rectified voltage produced via E-field reception, $V_{DCE}$. Allowing charging circuitry 156 to then choose $V_{DCB}$ over $V_{DCE}$ as its input voltage will allow such circuitry 156 to charge the battery 26 faster. Conversely, and as discussed further below, charging of the battery using $V_{DCE}$ is used as a last resort, and can occur passively. Charging circuitry 156 is well known in the art, and is capable of handling input voltages of different values, such as would be provides by $V_{DCE}$ and $V_{DCB}$. Although shown as comprising two different inputs to charging circuitry 156, it should be understood that $V_{DCE}$ and $V_{DCB}$ can be selected as a single input to the circuitry 156 using a switch controlled by control signals B and E (not shown). Of course, assertion of neither of control signals B or E would signify that the IPG 100 is not recognizing the receipt of any charging field from the base station 200 (or any other source such as the external charger 50), and will behave accordingly.

As discussed previously, the IPG 100 can back telemeter to the base station 200 charging information, such as the battery voltage ($V_{BAT}$) and coupling data, and such telemetry can also be controlled via control signals B and E. In this regard, and as shown in FIG. 8A, IPG 100 contains a RF transmitter/receiver 166 enabled by control signal E, and an LSK transmitter 160 enabled by control signal B. In other words, the IPG 100 decides through this scheme to communicate back to the base station 200 using the means (B-field or E-field) already established as reliable at the IPG 100 based on the fields it has received. LSK transmitter 160, if chosen using control signal B, uses the charging information to be telemetered to modulate a transistor 168 connected in parallel with coil 18. As noted earlier, this produces reflection in the coil 206 used in the base station to produce the B-field 304, which data can then be demodulated at the LSK receiver 220 in the base station (FIG. 7) to recover the charging information. Should the RF transmitter/receiver 166 be chosen via control signal E, the charging information will be modulated using a protocol suitable for broadcast via the E-field antenna 150, such frequency shift keying (FSK), phase shift keying (PSK), amplitude shift keying (ASK), etc. Such RF back telemetered data would then be received at the RF receiver 228 in the base station 200 (FIG. 7). Circuit 166 can also include corresponding demodulation circuits for receiving data from the base station 200, and in this regard, base station 200 can include an RF data transmitter coupled to antenna 204. However, such RF data transmission circuitry is not shown in the base station of FIG. 7, because in a simple embodiment of the technique, the E-field antenna 204 only broadcasts E-fields for the purpose of charging the IPG's battery 26, as explained further below.

RF transmitter/receiver 166 can operate at a frequency, $f_E'$, that is different from the transmission frequency of the E-field, $f_E$. Choosing a different frequency for $f_E'$ can prevent interference with the E-field 302 broadcast from the base station, and may allow for data reception at the base station E-field antenna 204 which is simultaneous with such broadcast. If a different frequency $f_E'$ is chosen for back telemetry, it may be advisable that such frequency not differ greatly from $f_E$; if an E-field at frequency $f_E$ is successfully received at the IPG 100, then it would be likely that transmission at a slightly different frequency $f_E'$ would likewise be received at the base station 200 without significant attenuation, etc. However, this is not strictly necessary, and $f_E$ can be significantly different from $f_E'$. Alternatively, E-field 302 and transmission of data from the RF transmitter/receiver 166 can be time multiplexed, in which case $f_E$ can equal $f_E'$.

Having described the charging circuitry of both base station 200 and IPG 100, discussion now turns to describing an exemplary method for charging the IPG 100 using the base station 200. In this example, the base station 200 automatically produces a charging field when turned on, and in particular, microcontroller 212 (FIG. 7) initially selects B-field charging as default. Using a B-field 304 as default means of charging is preferred if it can be accomplished, because it can generally provide more energy to the IPG 100, and hence can charge the battery 26 faster. Therefore, microcontroller 212 outputs K1=1 to set the base station for B-field charging: i.e., to set the signal generator 214 to output a frequency of $f_B$=80 kHz; to activate the switch 222 to couple the transmission circuitry to the coil 206; and to enable LSK receiver 220. At this point, the base station 200 is broadcasting the B-field 304, with the hope that an IPG 100 will receive this broadcast, and will acknowledge receipt by broadcasting either some sort of acknowledgment, or the charging information discussed earlier. Accordingly, microcontroller 212 waits for a certain period of time (e.g., one minute) to receive back telemetry data at the LSK receiver 220. During this "B period," the base station 200 can adjust the strength of the B-field 304 via the gain control signal with the hope of producing a B-field 304 that will eventually be large enough to be recognized by the IPG 100. For example, the base station may start with gain control at its smallest setting, and ramp the gain until it reaches a maximum level nearer to the end of the B period.

If IPG 100 is within range of the base station 200, its charging coil 18 (FIG. 8A) will receive the B-field 304. Assuming the B-field reception is strong enough, i.e., if $V_{DCB} > V_{thB}$, input X to the IPG's microcontroller 158 will be asserted. As discussed earlier, microcontroller 158 then acknowledges that B-field charging has commenced, and will set up the IPG 100 for charging by assertion of control signal B, which will enable charging circuitry 156 to chose $V_{DCB}$ as its input, and enable LSK transmitter 160. At that point, and as is typical in IPGs configured for B-field charging, the LSK transmitter 160 will start telemetering charging information ($V_{BAT}$; coupling data, etc.) back to the base station 200 via coil 18. Such charging information produces reflection in the base station's coil 206, and is decoded at the LSK receiver 220. Receipt of such data (or some other form of acknowledgment) informs the base station 200 that the IPG 100 is receiving the transmitted B-field 304, and that the base station 200 should stay in B-field default mode by continuing to assert K1=1. Moreover, the base station 200 can begin to interpret the received charging information, and modify the produced B-field 304 as necessary, i.e. by changing its magnitude via the gain control signal, and/or by changing its duty cycle. See, e.g., the above-incorporated '733 application.

If the battery 26 is fully charged, microcontroller 212, based on the reported value of $V_{BAT}$, can cease generating the B-field. At this point, the base station 200 can default to E-field charging, as discussed further below. Providing lower-power E-field charging can be beneficial should the IPG 100's battery 26 start to drain during use. If the IPG 100 however will not benefit from E-field charging because its battery 26 is full, it can simply disable charging circuitry 156 for example.

If the IPG 100 goes out of the range of the base station 200 or was never within range to start with, input X in the IPG 100 will equal '0'. As a result, microcontroller 158 in the IPG 100 will not acknowledge receipt of a B-field (or an E-field at this point), and so control signals B and E will be disabled, such that IPG 100 will not send any form of acknowledgement back to the base station 200. Eventually, e.g., once the one-minute B period has expired, the microcontroller 212 in the base station 200 will conclude that B-field charging cannot be accomplished, and will now default to E-field charging. Accordingly, microcontroller 212 now asserts K1=0, which sets the signal generator 214 to output a frequency of $f_E$=300 MHz; activates the switch 222 to couple the transmission circuitry to the antenna 204; and enables RF receiver 228.

In one embodiment, the base station 200 at this point will simply continue broadcasting the E-field 302 so long as it is powered on and without any communication from the IPG 100, that is, regardless of whether the IPG 100 can acknowledge and use the E-field for charging. This embodiment can be viewed as a simple, passive way to provide E-field charging: i.e., the low-power E-field 302 is produced, and it is hoped, but ultimately unknown, whether the E-field is of use to the IPG 100. Such an embodiment is simple, because it doesn't require any communications from the IPG 100 to the base station. Hence, RF transmitter/receiver 166 in the IPG 100, and RF receiver 228 in the base station 200, can be dispensed with. However, because this communication route is useful and provides additional flexibility in tailoring the generated E-field, it is discussed further below.

If the IPG 100 is within range of the E-field 302, but outside of the range of the B-field 304, signal input Y at the IPG's microcontroller 158 will be set to '1,' assuming E-field reception is strong enough, i.e., if $V_{DCE} > V_{thE}$. At that point, microcontroller 158 will set up the IPG 100 for charging by assertion of control signal E, which will enable charging circuitry 156 to chose $V_{DCE}$ as its input, and enable RF transmitter/receiver 166. The battery 26 will then begin charging, but as discussed above at a slower rate due to the relatively small value of $V_{DCE}$. RF transmitter/receiver 166 can then transmit the charging information back to the base station 200 via its antenna 150. At the base station 200, such charging information is received at antenna 204, decoded at RF receiver 228, and used appropriately by the microcontroller 212. For example, the microcontroller 212 can use the charging information to modify the strength of the generated E-field 302 via the gain control signal for example. Alternatively, the microcontroller 212 could suspend generation of the E-field 302 if $V_{BAT}$ informs that the battery 26 is fully charged. However, and as discussed above, in another embodiment, the base station 200 can simply continue to generate the lower-power E-field 200 even if the battery is currently fully charged, in the off chance that the battery 26 depletes and will eventually be able to use the E-field for charging once again.

Charging of a patient's IPG battery 26 by E-field is a significant benefit due to its relatively long effectiveness (e.g., >1 m), and even though it is imparts a relatively low amount of power to the IPG 100, such power can still be put to use to recharge the battery 26 if the patient is in the vicinity of the E-field, even in passing.

In a preferred embodiment, the base station 200 can periodically assess whether B-field charging is available, and can switch to that mode if so. This is reasonable because an IPG 100 initially outside of the range of the base station 200 may come within range, because the patient has moved, is now lying down in bed, etc. Accordingly, periodically, e.g., every 15 minutes or so, the base station 200 can revert to the B period discussed above: it can assert K1=1 for a period of time to enable B-field charging, and adjust the strength of the B-field 304 to see if the IPG 100 acknowledges B-field reception. If so, the base station 200 can continue production of the higher-power B-field 304. If not, the base station 200 can once again start generating the lower-power E-field 302 at the expiration of the B period.

Figure 9:
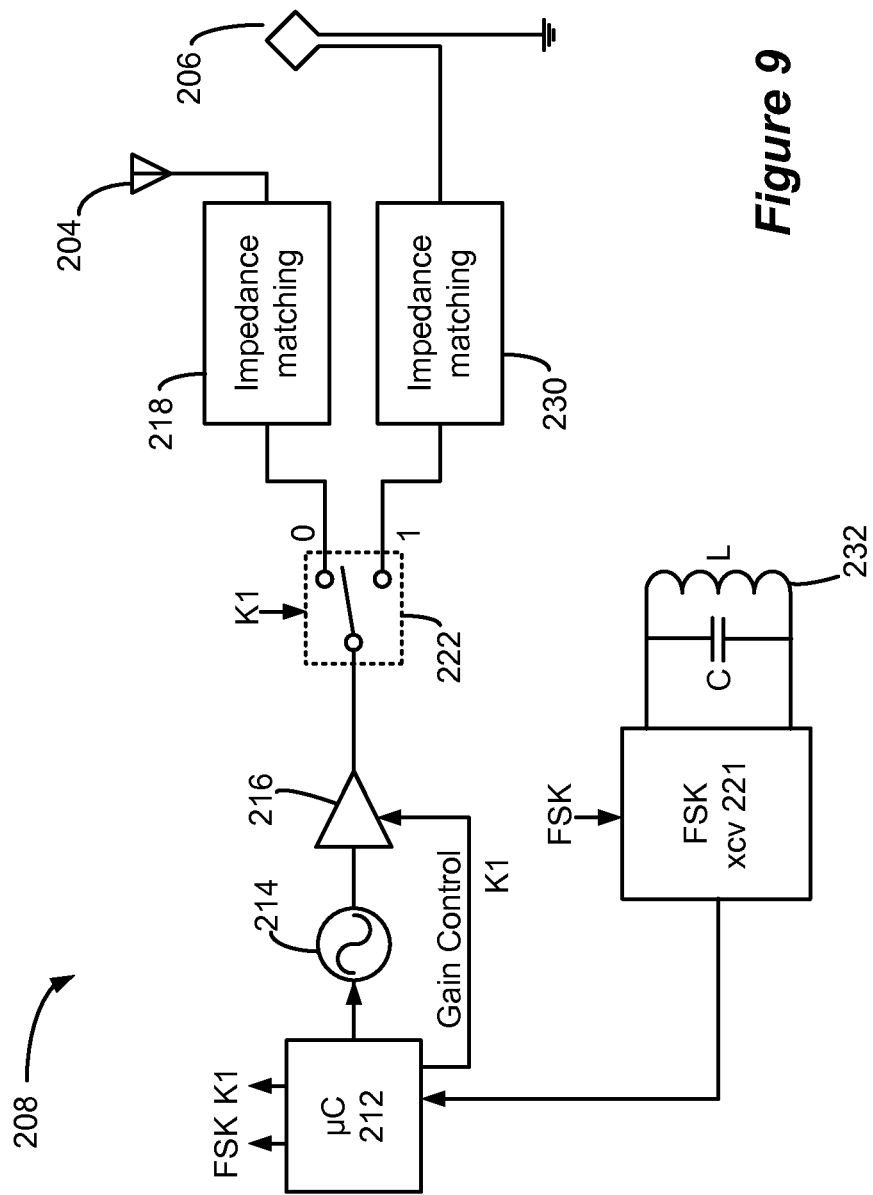
FIGS. 9 and 10 show alternative schematics of a base station and the IPG having an additional communication channel and hardware.
Figure 10:
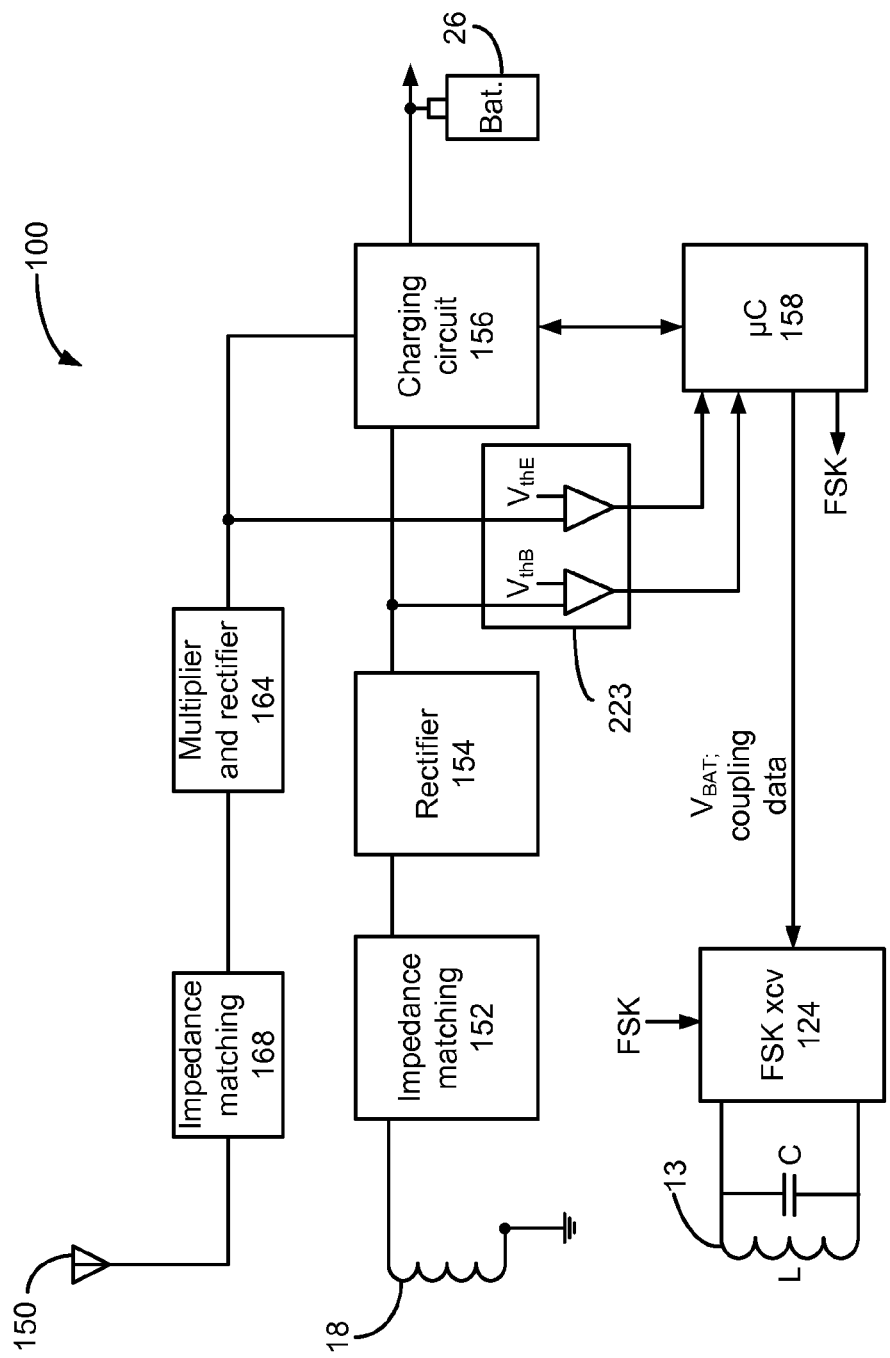

FIGS. 9 and 10 respectively show alternative embodiments for the base station 200 and IPG 100, where the back telemetry is carried out using hardware and a communication channel that is separate from those used to charge the IPG. Thus, FIG. 9 shows the base station with an additional antenna 232, and FIG. 10 shows the IPG having an additional antenna 13. In this example, the antennas 232 and 13 are shown as coils, and communicate by magnetic induction. This is convenient, and is considerate of legacy system design, because the antenna 13 already exists in the IPG 100 and is traditionally used to communicate with an external controller 12 (FIG. 2) as discussed in the Background. As explained earlier, such communication between antennas 232 and 13 could occur using an FSK protocol, and thus FSK transceivers 221 and 124 are shown coupled to antennas 232 and 13. Such communication can be bi-directional, or one-way from the IPG 100 to the base station for the purpose of telemetering the charging information. By using the pre-existing coil 13 in the IPG 100 to also communicate with the base station 200 during charging, system functionality can be expanded without the need to modify existing communication circuitry in the IPG 100. However, is it not strictly necessary to use the pre-existing communications coil 13 in the IPG, and instead a separate dedicated RF or magnetic-induction antenna could be added to the IPG 100 and base station 200 instead. Because this means of transmission between the IPG 100 and the base station is not tied to the communication channels used for charging, note that the FSK transceivers 221 and 124 can be enabled using control signals (FSK) having no connection to the control signals used in the base station 200 or IPG 100 indicative of whether those devices are operating in a B-field or E-field mode (i.e., FSK is independent of control signal K1 in the base station, or control signals B and E in the IPG 100).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a battery;
   a first antenna configured to receive an electric field for charging the battery;
   a second antenna configured to receive a magnetic field for charging the battery; and
   a microcontroller for determining whether either or both of the electric field and the magnetic field have been received at the first or second antennas respectively, and for issuing at least one control signal enabling charging of the battery either by the electric field or the magnetic field.

2. The device of claim 1, further comprising a first rectifier coupled to the first antenna for producing a first DC voltage, and a second rectifier coupled to the second antenna for producing a second DC voltage.

3. The device of claim 2, wherein the microcontroller determines whether either or both of the electric field and the magnetic field have been received at the first or second antennas respectively using first and second DC voltages.

4. The device of claim 2, further comprising charging circuitry, wherein the charging circuitry is responsive to the at least one control signal to select either the first DC voltage or the second DC voltage as the power source for charging the battery.

5. The device of claim 1, wherein the at least one control signal enables a transmitter for transmitting charging information from the implantable medical device.

6. The device of claim 5, wherein the transmitter transmits the charging information from either the first or second antenna.

7. The device of claim 1, wherein the charging information comprises a voltage of the battery.

8. The device of claim 1, wherein the first antenna comprises an electrode lead coupled to an electrode for providing stimulation to a patient's tissue.

9. An implantable medical device, comprising:
   a battery;
   a first antenna configured to receive a first field for charging the battery, wherein the first field is less than or equal to 100 kHz;
   a second antenna configured to receive a second field for charging the battery, wherein the second field has a frequency ranging from 1 MHz to 10 GHz; and
   a microcontroller for determining whether either or both of the first field and the second field have been received at the first or second antennas respectively, and for issuing at least one control signal enabling charging of the battery either by the first field or the second field.

10. The device of claim 9, further comprising a first rectifier coupled to the first antenna for producing a first DC voltage, and a second rectifier coupled to the second antenna for producing a second DC voltage.

11. The device of claim 10, wherein the microcontroller determines whether either or both of the first field and the second field have been received at the first or second antennas respectively using first and second DC voltages.

12. The device of claim 10, further comprising charging circuitry, wherein the charging circuitry is responsive to the at least one control signal to select either the first DC voltage or the second DC voltage as the power source for charging the battery.

13. The device of claim 9, wherein the at least one control signal enables a transmitter for transmitting charging information from the implantable medical device.

14. The device of claim 13, wherein the transmitter transmits the charging information from either the first or second antenna.

15. The device of claim 9, wherein the charging information comprises a voltage of the battery.

16. The device of claim 9, wherein the first antenna comprises an electrode lead coupled to an electrode for providing stimulation to a patient's tissue.

17. The device of claim 9, wherein the first field comprises an electric field, and wherein the second field comprises a magnetic field.

* * * * *